United States Patent [19]

Mittendorf et al.

[11] Patent Number: 5,849,924

[45] Date of Patent: Dec. 15, 1998

[54] HIGHLY SELECTIVE PROCESS FOR THE PREPARATION OF ENANTIOMERICALLY PURE PHENYL-SUBSTITUTED 1,4-DIHYDROPYRIDINE-3,5-DICARBOXYLIC ACID DERIVATIVES

[75] Inventors: Joachim Mittendorf; Peter Fey; Bodo Junge, all of Wuppertal; Johannes Kaulen, Boffzen; Kai van Laak, Köln, all of Germany; Heinrich Meier, Kobe, Japan; Rudolf Schohe-Loop, Wuppertal, Germany

[73] Assignee: Bayer Aktiengesellscahft, Leverskusen, Germany

[21] Appl. No.: 896,275

[22] Filed: Jul. 16, 1997

Related U.S. Application Data

[62] Division of Ser. No. 563,725, Nov. 28, 1995, Pat. No. 5,700,948.

[30] Foreign Application Priority Data

Dec. 5, 1994 [DE] Germany .......................... 44 43 168.6

[51] Int. Cl.⁶ .................................................. C07D 211/80
[52] U.S. Cl. ............................................................. 546/342
[58] Field of Search ............................................... 546/342

[56] References Cited

U.S. PATENT DOCUMENTS 3,932,646  1/1976  Meyer et al. ........................... 514/356

FOREIGN PATENT DOCUMENTS 0160451  11/1985  European Pat. Off. .
0166296   1/1986  European Pat. Off. .

OTHER PUBLICATIONS

V.S. Goldman, et al., Angew. Chem., vol. 103, pp. 1587–1605, (1991).

A. Bernardi, et al., Tetrahedron Letters, vol. 31, No. 34, pp. 4949–4952, (1990).

W.J. Klaver, et al., J. Am. Chem. Soc., vol. 111, pp. 2588–2595, (1989).

*Primary Examiner*—Zinna Northington Davis
*Attorney, Agent, or Firm*—Sprung Kramer Schaefer & Briscoe

[57] ABSTRACT

The present invention relates to a new highly selective process for the preparation of enantiomerically pure halogeno-phenyl-substituted 1,4-dihydropyridine-3,5-dicarboxylic esters of the general formula (I)

$$R^1O_2C \overset{R^2}{\underset{H_3C\underset{\underset{H}{N}}{}CH_3}{\overset{*}{\diagup\!\!\!\diagdown}}} CO_2R^3 \quad (I)$$

*R und S in which $R^1$ to $R^3$ have the meanings given in the description.

1 Claim, No Drawings

HIGHLY SELECTIVE PROCESS FOR THE PREPARATION OF ENANTIOMERICALLY PURE PHENYL-SUBSTITUTED 1,4-DIHYDROPYRIDINE-3,5-DICARBOXYLIC ACID DERIVATIVES

This application is a divisional of application Ser. No. 08/563,725, filed Nov. 28. 1995 now U.S. Pat. No. 5,700,948.

The present invention relates to a new selective process for the preparation of enantiomerically pure phenyl-substituted 1,4dihydropyridine-3,5-dicarboxylic acid derivatives.

The publication Angew. Chem. 103, 1991, 1587–1605 describes the high importance of the absolute stereochemistry of 1,4-dihydropyridines for their pharmacological action as calcium antagonists or calcium agonists and provides a list of the processes available to date for preparing them in enantionmerically pure form. All these processes emphasize the separation of diastereomeric esters using chiral pool auxiliaries, the selection of which being essentially a trial-and-error method with regard to the substantial difficulties often encountered in their preparation and the introduction and elimination into, or from, the molecules. In particular the elimination of a large number of auxiliaries is frequently complicated from the technical and chemical point of view, and this, in turn, results in a decreased yield.

Suprisingly, there has now been found a highly selective method by using maleimides as auxiliaries.

The invention relates to a new highly selective process for the preparation of enantiomerically pure phenyl-substituted 1,4-dihydropyridine-3,5-dicarboxylic acid derivatives of the general formula (I)

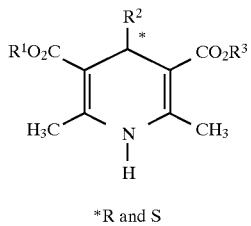

(I)

*R and S in which $R^1$ and $R^3$ are identical or different and represent straight-chain or branched alkyl having up to 8 carbon atoms which is optionally substituted by straight-chain or branched alkoxy having up to 6 carbon atoms or hydroxyl, or represent cycloalkyl having 3 to 7 carbon atoms, and $R^2$ represents the radical

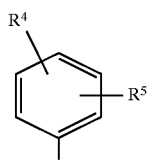

in which $R^4$ and $R^5$ are identical or different and denote halogen, cyano, ethinyl, trifluoromethoxy, methylthio, nitro, trifluoromethyl or straight-chain or branched alkyl, alkenyl, alkinyl or alkoxy having up to 4 carbon atoms, and one of the substituents optionally represents hydrogen, and their salts, characterized in that the enantiomerically pure benzylidene compounds of the general formula (II) or the benzylidene compounds of the general formula (IIa)

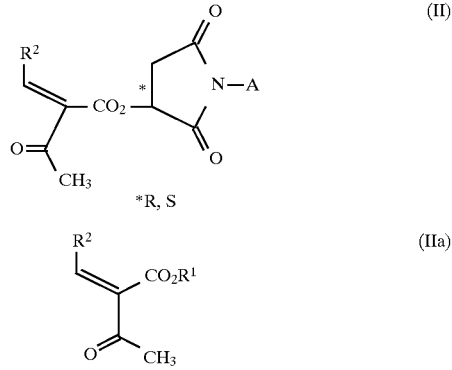

in which $R^1$ and $R^2$ have the abovementioned meanings and

A represents hydrogen or straight-chain or branched alkyl having up to 8 carbon atoms, or represents phenyl or benzyl which are optionally up to trisubstituted by identical or different substituents from the series consisting of hydroxyl, nitro, halogen, cyano, carboxyl, trifluoromethyl, trifluoromethoxy, straight-chain or branched alkoxy having up to 6 carbon atoms or by a group of the formula —$NR^6R^7$ or —$SO_2R^8$ in which $R^6$ and $R^7$ are identical or different and denote hydrogen, phenyl or straight-chain or branched alkyl having up to 5 carbon atoms and $R^8$ denotes straight-chain or branched alkyl having up to 4 carbon atoms or phenyl, are converted, by reaction, in the case of the enantiomerically pure benzylidene compounds of the general formula (II), with aminocrotonic esters of the general formula (III) and, in the case of the benzylidene compounds of the general formula (IIa), with the corresponding enantiomerically pure aminocrotonic esters of the general formula (IIIa)

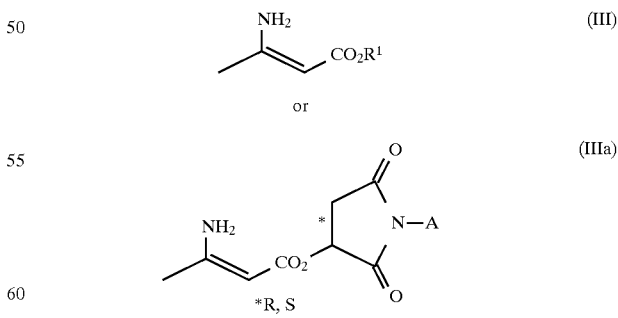

in which $R^1$ and A have the abovementioned meanings in inert solvents, if appropriate in the presence of a base, to the diastereomerically pure 1,4-dihydropyridines of the general formulae (IVa) and (IVb)

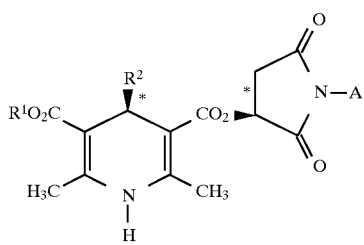

(IVa)

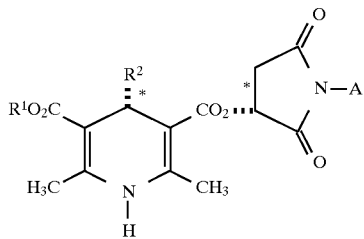

(IVb)

in which

R¹, R² and A have the abovementioned meanings and the maleimide radical subsequently eliminated with weak bases under mild conditions, if appropriate isolating the free acid, and the carboxyl function is esterified by customary methods.

The process according to the invention can be illustrated by way of example by the formulae of the following scheme:

[A]

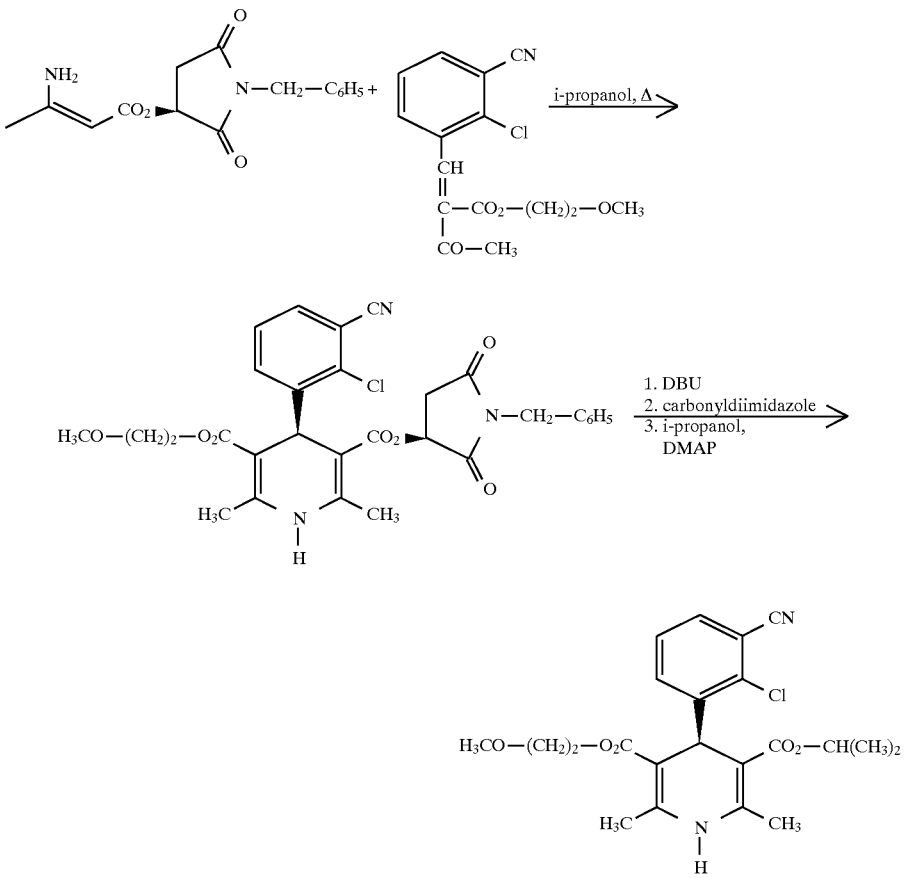

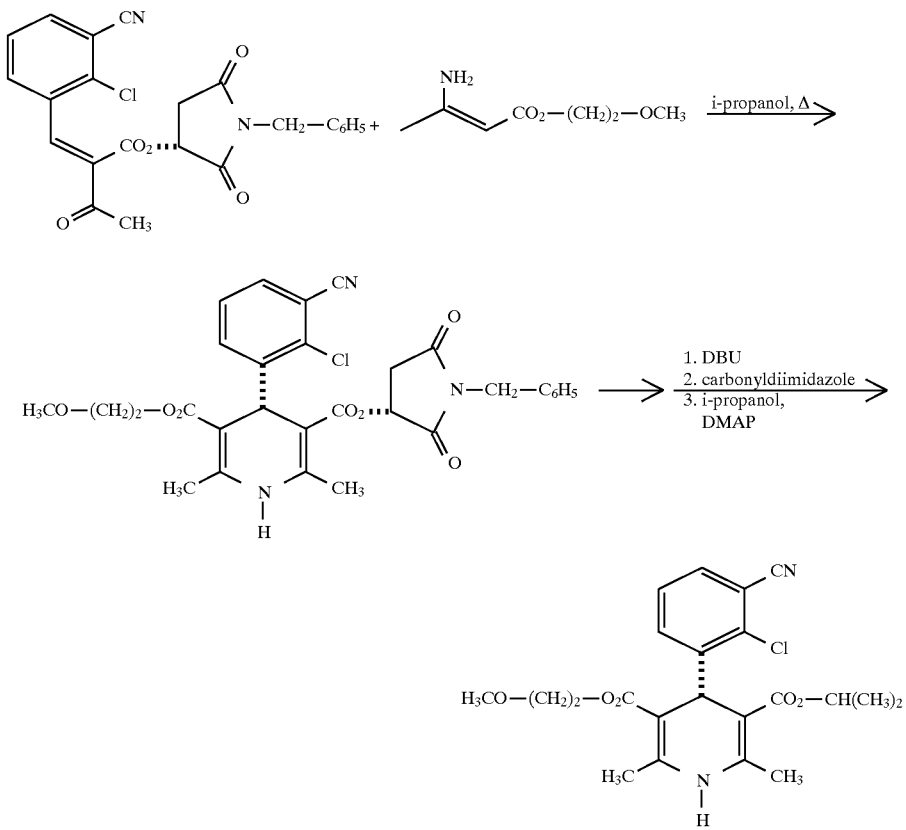

Surprisingly, the process according to the invention gives the chiral compounds of the general formula (I) in a sophisticated manner in very high enantiomeric purity combined with very high yields.

In contrast to the abovementioned prior art, the process according to the invention provides a highly enantioselective route for the synthesis of enantiomerically pure substituted 4-phenyl-1,4-dihydropyridine-3,5-dicarboxylic acid derivative by using maleimide radicals in the compounds of the general formula (IV) and (IVa) as auxiliaries, these existing in both enantiomerically pure forms. The maleimides, in turn, can be obtained from the corresponding (R)— or (S)— maleic acid via a single, simple chemical reaction. The process according to the invention is also distinguished by the fact that, in contrast to the prior art, the maleimides, as auxiliaries, can be introduced readily into the benzylidene compounds of the general formula (II) or into the aminocrotonic esters of the general formula (IIIa). Moreover, the maleimide radicals can be eliminated selectively from all compounds in a highly sophisticated manner under very mild conditions, using weak bases. Moreover, simply and systematically varying the radical A in the maleimides of the general formulae (IV) and (IVa) allows the problem to be solved in an optimal fashion with a view to the dihydropyridine in question. Due to the rigid, cyclic structure of the maleimides, the corresponding diastereomerically pure dihydropyridines of the general formula (IV/IVa) not only crystallize in very high yields but are also distinguished by substantially different crystallization behaviours.

These advantages, which, in the end, also make possible the very high yields of the compounds of the general formula (I) according to the invention, are not achieved by any known auxiliary.

A further advantage of the process according to the invention, in particular with a view to costs, is the fact that the entire reaction sequence is very short and presents few complications and that even the various intermediates can be obtained in very good yields and with high diastereomeric or enantiomeric purity.

The process according to the invention is suitable in principle for the synthesis of enantiomerically pure dihydropyridine-3,5-dicarboxylic acid derivatives.

Suitable solvents for the reaction of the compounds of the formulae (IIa) and (IIIa) are generally all inert organic solvents which do not undergo changes under the reaction conditions. These preferably include alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric triamide or dimethylformamide, or acetic acid or esters, such as ethyl acetate, or halogenated hydrocarbons, such as methylene chloride, carbon tetrachloride or hydrocarbons such as benzene, xylene or toluene. Equally, it is possible to use mixtures of the abovementioned solvents. Isopropanol is preferred.

The reaction temperatures can be varied within a substantial range. In general, the process is carried out between 20° C. and 120° C., preferably between 60° C. and 90° C.

The reactions can be carried out under atomospheric pressure, but also under elevated or reduced pressure (for example 0.5 to 80 bar). In general, it is carried out under atmospheric pressure.

Suitable solvents for the reaction of the compounds of the formulae (II) and (III) are ethyl acetate or isopropanol.

Some of the compounds of the general formula (IIa) are known or can be prepared by customary methods, for example by reacting the corresponding aldehydes with 2-alkoxyalkyl acetoacetates.

The compounds of the general formula (III) are known per se.

The enantiomerically pure benzylidene compounds of the general formula (II) are new and can be prepared by reacting aldehydes of the general formula (V)

$$R^2\text{—CHO} \qquad (V)$$

in which

R$^2$ has the abovementioned meaning with enantiomerically pure acetoacetic esters of the general formula (VI)

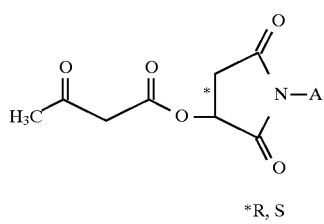

*R, S in which

A has the abovementioned meaning in inert solvents and in the presence of a base and of a carboxylic acid.

Suitable solvents for the first step are all inert organic solvents which do not undergo changes under the reaction conditions. These preferably include alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric triamide or dimethylformamide, or acetic acid or esters, such as ethyl acetate, or halogenated hydrocarbons, such as dichloromethane, carbon tetrachloride or hydrocarbons such as benzene or toluene. Equally, it is possible to use mixtures of the abovementioned solvents. Dichloromethane is preferred.

Bases which are preferably suitable for the first step are cyclic amines, such as, for example, piperidine, $C_1$–$C_3$-tri- and dialkylamines, such as, for example, di- and triethylamine or pyridine or dimethylaminopyridine. Piperidine is preferred.

In general, the base is employed in an amount of 0.01 mol to 0.10 mol, preferably from 0.05 mol to 0.08 mol, per mole of the aldehyde.

Preferably suitable acids are $C_1$–$C_4$-alkylcarboxylic acid, such as, for example, acetic acids.

In general, the acid is employed in an amount of 0.01 mol to 0.10 mol, preferably from 0.05 mol to 0.08 mol, per mole of the aldehyde.

The reaction temperature in the first step can be varied within a substantial range. In general, the process is carried out in the range from 20° C. to 120° C., preferably from 30° C. to 60° C.

The processes can be carried out under atmospheric pressure, elevated pressure or reduced pressure (for example from 0.5 to 5 bar), preferably under atmospheric pressure.

The aldehydes of the general formula (V) are known or can be prepared by customary methods.

The enantiomerically pure compounds of the general formula (VI) are new and can be prepared by reacting (S)— or (R)— maleimides of the general formula (VII)

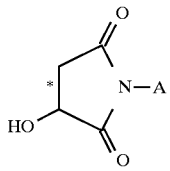

*R, S in which

A has the abovementioned meaning with diketene or diketene/acetone addition product (2,2, 6-trimethyl-1,3-dioxin4-one) in inert solvents.

Generally suitable solvents are hydrocarbons, such as, for example, benzene, toluene or xylene. Toluene is preferred.

The reactions are carried out in a temperature range from 90° C. to 140° C., preferably from 100° C. to 110° C.

The reactions are generally carried out under atmospheric pressure. However, it is also possible to carry out the reactions under superatmospheric or subatmospheric pressure (for example in the range from 0.5 to 5 bar).

Some of the enantiomerically pure imides of the general formula (VII) are known [cf., for example, THL 1990, 4949; J. Am. Chem. Soc., 2589, 1989] or can be prepared by reacting (S)—(-)- or (R)—(-)-maleic acid with the corresponding amines in one of the abovementioned solvents, preferably xylene, in a temperate range from 100° C. to 180° C., preferably from 130° C. to 150° C.

Diketene and 2,2,6-triethyl-1,3-dioxin-4-one are known.

The enantiomerically pure aminocrotonic esters of the general formula (IIIa) are new and can be prepared, for example, by adding ammonia or ammonium salts in situ in the preparation of the abovementioned acetoacetic esters of the general formula (VI).

Suitable solvents are those which have been mentioned in the preparation of the compound of the general formula (VI). The reaction with the ammonium salts is carried out in toluene in a water separator under reflux.

The reactions are carried out in a temperature range from 50° C. to 120° C., preferably from 5° C. to 80° C.

The reactions are generally carried out under a subatmospheric pressure of 0.1 to 0.5 bar. However, it is also possible to carry out the reactions under atmospheric or superatmospheric pressure (for example in the range from 1 to 5 bar).

Suitable ammonium salts are generally ammonium salts of organic or inorganic acids, such as, for example ammonium acetate or ammonium formate. Ammonium acetate is preferred.

The enantiomerically pure compounds of the general formula (IV) are new and can be prepared as described above.

The substituted pyrrolidine-2,5-dion-3-yl radical is eliminated from the enantiomerically pure 1,4-dihydropyridines of the general formula (IV) in one of the abovementioned inert solvents. Preferred are ethyl acetate, tetrahydrofuran or mixtures of these two.

Suitable bases are generally alkali metal carbonates, such as, for example, sodium carbonate or potassium carbonate, or organic bases, such as trialkylamines, for example triethylamine, N-ethylmorpholine, N-methylpiperidine or diisopropylethylamine or dimethylaminopyridine, 1,8-diazabicyclo[5.4.0]undec-7-ene (DBU) or 1,5-diazabicyclo[4.3.0]non-5-ene (DBN). 1,8-diazabicyclo[5.4.0]undec-7-ene is preferred.

The base is applied in an amount of 1 mol to 5 mol, preferably 1 mol to 2 mol, in each case per mole of the enantiomerically pure compounds of the general formula (IV).

The reaction is carried out in a temperature range from 0° C. to 50° C., preferably at room temperature.

The reaction is generally carried out under atmospheric pressure. However, it is also possible to carry out the reaction under superatmospheric or subatmospheric pressure (for example in the range from 0.5 to 5 bar).

Without isolating the free enantiomerically pure acid, the compounds of the general formulae (IV) or (IVa) are subsequently converted to the enantiomerically pure compounds of the general formula (VIII)

$$R^1O_2C \underset{H_3C}{\overset{R^2}{\underset{N}{\bigvee}}} CO-D \quad *R, S \quad (VIII)$$

in which
R$^1$ and R$^2$ have the abovementioned meanings
and
D represents an activating radical, for example imidazolyl, by means of activation with an auxiliary in one of the abovementioned solvents in the presence of ethyl acetate, and, in a last step, the products are reacted with a suitable alcohol (R$^3$—OH) in the presence of one of the abovementioned bases, preferably N,N-dimethylaminopyridine, at the reflux temperature of the alcohol in question, to give the enantiomerically pure compounds of the general formula (I) according to the invention.

Auxiliaries which are preferably employed for activating the carboxylic acid are condensing agents. Condensing agents which are preferably employed are the customary condensing agents, such as carbodiimides, for example N,N'-diethyl-, N,N'-dipropyl-, N,N'-diisopropyl-, N,N'-dicyclohexylcarbodiimide, N-(3-dimethylaminoisopropyl-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate or 2-tert-butyl-5-methyl-isoxazolium perchlorate, or acylamino compounds, such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphonate. N,N'-di-cyclohexylcarbodiimide and carbonyldiimidazole are preferred.

In general, the auxiliaries are employed in an amount of 1 mol to 3 mol, preferably 1 mol to 1.5 mol, in each case per mole of the free carboxylic acid.

The processes can be carried out under atmospheric pressure, elevated or reduced pressure (for example from 0.5 to 5 bar), preferably under atmospheric pressure.

The activated enantiomerically pure 1,4-dihydropyridines of the general formula (VIII) are known or can be prepared as described above.

Preferred enantiomerically pure compounds of the general formula (I) which are prepared by the process according to the invention are those
in which
R$^1$ and R$^3$ are identical or different and represent straight-chain or branched alkyl having up to 8 carbon atoms which is optionally substituted by straight-chain or branched alkoxy having up to 5 carbon atoms or hydroxyl, or represents cyclopropyl, cyclopentyl, cyclohexyl or cycloheptyl, and R$^2$ represents the radical $$\underset{}{\bigotimes}\!\!-\!R^5 \quad R^4$$

in which
R$^4$ and R$^5$ are identical or different and in each case denote fluorine, bromine, chlorine, cyano, ethinyl, trifluoromethoxy, methyl, nitro, methylthio, trifluoromethyl or straight-chain or branched alkoxy having up to 3 carbon atoms, and, if appropriate, one of the substituents represents hydrogen,
and salts thereof.

Particularly preferred compounds of the general formula (I) which are prepared by the process according to the invention are those:
in which
R$^1$ and R$^3$ are identical or different and represent straight-chain or branched alkyl having up to 8 carbon atoms which is optionally substituted by methoxy or hydroxyl, or represents cyclopropyl, cyclopentyl, cyclohexyl or cycloheptyl, and R$^2$ represents the radical $$\underset{}{\bigotimes}\!\!-\!R^5 \quad R^4$$

in which
R$^4$ and R$^5$ are identical or different and denote fluorine, chlorine, cyano, ethinyl, trifluoromethoxy, methyl, methylthio, nitro, trifluoromethyl or straight-chain or branched alkoxy having up to 3 carbon atoms, and, if appropriate, one of the substituents represents hydrogen,
and salts thereof.

Enantiomerically pure compounds which are very particularly preferably prepared by the process according to the invention are (4R)- and (4S)-isopropyl-(2-methoxyethyl)-4-(2-chloro-3-cyano-phenyl)-1,4-dihydro-2,6-dimethyl-pyridine-3,5-dicarboxylate.

The process according to the invention allows access to the enantiomerically pure halogenphenyl-substituted 1,4-dihydropyridines of the general formula (I), which are valuable cerebrally active pharmaceuticals, in a highly enantioselective manner combined with a very high yield.

STARTING COMPOUNDS

Example I (Formula VI)

(3S)-1-Benzyl-3-(3-oxobutyryloxy)-pyrrolidine-2,5-dione 2,2,6-Trimethyl-1,3-dioxine4-one (6.6 g, 4.38 mmol, 95% pure) is added dropwise to a solution of N-benzyl-(S)- maleimide (9.0 g, 43.8 mmol) [THL 1990, 4949] in xylene (18 ml) at 130° C. The acetone which forms is distilled off from the reaction mixture. Stirring is continued for 2 hours at 130° C., the reaction solution is cooled to 50° C., and the solvent is stripped off in vacuo. The residue is purified by column chromatography on silica gel (eluent: diethyl ether). After the product fractions have been concentrated, 11.8 g (93%) of the title compound are obtained.

$^1$H NMR (CDCl$_3$): δ=2.28 (s, 3H); 2.77 (dd, J=18 Hz, 5 Hz, 1H); 3.19 (dd, J=18 Hz, 8 Hz, 1H); 3.56 (s, 2H); 4.68 (AB system, 2H); 5.49 (dd, J=8 Hz, 5 Hz, 1H); 7.25–7.42 ppm (m, 5H); enol H: weak singulet at 11.68 ppm).

Example II (3S)-3-(3-Aminocrotonyloxy)-1-benzyl-pyrrolidine-2,5-dione

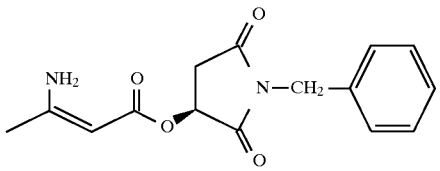

A suspension of N-benzyl-(S)-maleimide (1700 g, 8.28 mol) in toluene (6.8 l) is heated at 105° C., and 2,2,6-trimethyl-1,3-dioxin-4-one (85% pure, 1447 g, 8.65 mol) are run in in the course of approximately 20 minutes, the acetone which forms being distilled off together with toluene. Stirring is continued for 2 hours at 100–105° C., more acetone/toluene being distilled off. Toluene (1 l) is run into the reaction solution, and the batch is cooled to 70° C. After ammonium acetate (1207 g, 15.7 mol) has been added, the mixture is refluxed in a water separator at 65° C. and 250–300 mbar for 3 hours. Ethyl acetate (3.4 l) is run in, the batch is cooled to room temperature and washed with saturated aqueous NaHCO$_3$ solution, the organic phase is dried over Na$_2$SO$_4$, and the solvent is distilled off in vacuo at 35–40° C. The residue is taken up in isopropanol (4.2 l), and the solvent is distilled off in vacuo at 25–65° C. The residue is again taken up in isopropanol (2.5 l). The suspension is refluxed, during which process the solid dissolves. After the mixture has cooled to 5–7° C., water (1.8 l) is run in, precipitated product is filtered off and washed with isopropanol/water (1:1, 3.4 l), and the product is dried in vacuo at 50° C.

Yield 1990 g (83%)

m.p.: 104–105° C.

$^1$H NMR (CDCl$_3$): δ1.94 (s, 3H); 2.71 (dd, J=18 Hz, 5 Hz, 1H); 3.12 (dd, J=18 Hz, 8 Hz, 1H); 4.57 (s, 1H); 4.71 (AB system, 2H); 4.74 (s, broad, 1H); 5.40 (dd, J=8 Hz, 5 Hz, 1H); 7.20–7.44 (m, 5H); 7.88 ppm (s, broad, 1H).

Example III (Formula II)

1-Benzylpyrrolidine-2,5-dion-3-yl (3'S)-2-acetyl-3-(2-chloro-3-cyanophenyl)-2-propenoate

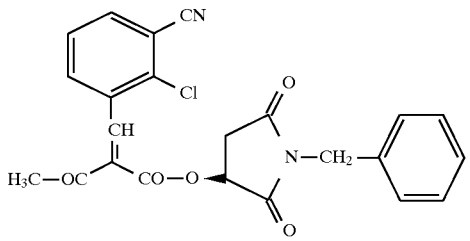

A solution of the compound of Example I (12.6 g, 43.6 mmol) and 2-chloro-3-cyano-benzaldehyde (7.2 g, 43.6 mmol) in dichloromethane (80 ml) is treated with piperidine (246 mg, 2.8 mmol) and glacial acetic acid (168 mg, 2.8 mmol), and the mixture is refluxed in a water separator for 18 hours. After the dichloromethane solution has cooled to room temperature, it is washed with water (40 ml), dried over Na$_2$SO$_4$ and concentrated in vacuo. The residue is purified by column chromatography on silica gel (eluent: ether). After concentrating the product fractions, 13.0 g (68%) of the title compound are obtained as a mixture of E/Z isomers.

$^1$H NMR (CDCl$_3$): δ=2.30, 2.51 (2s, 3H); 2.70–2.87 (m, 1H); 3.08–3.33 (m, 1H); 4.63–4.80 (m, 2H); 5.51–5.69 (m, 1H); 7.27–7.92 (m, 9H).

Example IV (Formula IV)

(4R,3'S)-(1-Benzyl-pyrrolidine-2,5-dion-3-yl)-(2-methoxyethyl)-4-(2-chloro-3-cyano-phenyl)-1,4-dihydro-2,6-dimethyl-pyridine-3,5-dicarboxylate

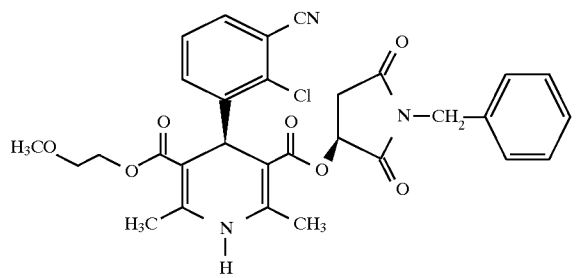

Variant A

The compound of Example II (80.0 g, 0.244 mol) and 2-methoxyethyl 2-acetyl-3-(2-chloro-3-cyano-phenyl)-2-propenoate (83.29 g, 0.243 mol) are treated with isopropanol (1100 ml), and the mixture is refluxed for 8.5 hours. It is cooled to room temperature, and the crude product, which has precipitated, is washed twice using in each case 100 ml of isopropanol and dried in vacuo at 40° C. The crude product is suspended in ethyl acetate (200 ml), and the supension is refluxed for 1 hour. After the mixture has cooled to room temperature, the product is filtered off, washed with ethyl acetate (40 ml) and dried in vacuo at 50° C.

Yield: 57.8 g (41%)
Diastereomeric excess ≧99.5% (HPLC, Chiracel OD-H)
m.p.: 239–240° C.
$^1$H NMR (d$_6$DMSO): δ=2.26 (s, 6H); 2.68 (dd, J=18 Hz, 5 Hz, 1H); 3.09 (dd, J=18 Hz, 8 Hz, 1H); 3.16 (s, 3H);

3.37–3.50 (m, 2H); 3.95–4.12 (m, 2H); 4.52, 4.64 (AB signal, $J_{AB}$=15 Hz, 2H); 5.25 (s, 1H); 5.53 (dd, J=8 Hz, 5 Hz, 1H); 7.22–7.77 (m, 8H).

Variant B (via II and III)

The compound of Example III (3.0 g, 6.9 mmol) and 2-methoxyethyl 3-aminocrotonate (1.1 g, 6.9 mmol) are treated with ethyl acetate (38 ml), and the mixture is refluxed for 5 hours. The product which has precipitated is filtered off, washed with ethyl acetate (3 ml) and dried in vacuo at 40° C.

Yield: 1.3 g (33%)

Diastereomeric excess ≧99.5% (HPLC, Chiracel OD-H)

Example V (4R)-Imidazolyl-2-methoxyethyl-4-(2-chloro-3-cyano-phenyl)-1,4-dihydro-2,6-dimethyl-pyridine-3,5-dicarboxylate

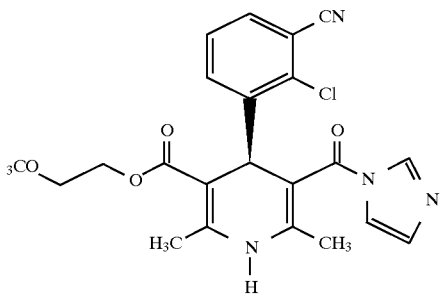

The compound of Example IV (73.9 g, 0.128 mol) is suspended in ethyl acetate (480 ml) and tetrahydrofuran (96 ml), and the suspension is treated with 1,8-diazabicyclo [5.4.0]undec-7-ene (DBU, 29.0 ml, 0.192 mol) and stirred at room temperature for 12 hours. Then, 1N HCl (300 ml) is added, and the mixture is stirred vigorously for 15 minutes. The ethyl acetate phase is separated off, washed in each case once using 1N HCl (150 ml) and saturated aqueous NaCl solution and dried over $Na_2SO_4$. The solvent is stripped off in vacuo and the residue is taken up in ethyl acetate (420 ml). After an addition of N,N'-carbonyldiimidazole (25.0 g, 0.154 mol), the mixture is stirred at room temperature for 12 hours and at 0–5° C. for 30 minutes. The product which has precipitated is filtered off, washed with ethyl acetate (25 ml) and dried in vacuo.

Yield: 42.6 g (76%)

m.p.: 180° C.

$^1$H NMR (CDCl$_3$): δ=1.90 (s, 3H); 2.48 (s, 3H); 3.22 (s, 3H); 3.40–3.52 (m, 2H); 4.10 (t,2H); 5.58 (s, 1H); 6.02 (s, 1H); 7.08 (d, 1H); 7.25–7.58 (m, 4H); 7.91 (s, 1H).

DIHYDROPYRIDINES OF THE FORMULA (I)

Example I (4R)-Isopropyl 2-methoxyethyl 4-(2-chloro-3-cyano-phenyl)-1,4-dihydro-2,6-dimethyl-pyridine-3,5-dicarboxylate

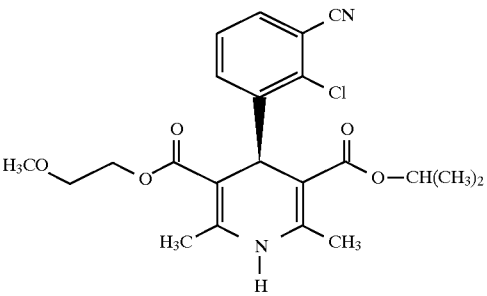

The compound of Example V (73.2 g, 166 mmol) and N,N-dimethylaminopyridine (0.93 g, 7.6 mmol) are refluxed in isopropanol (530 ml) for 20 hours. The reaction mixture is slowly cooled to 0–5° C. and stirred at 0–5° C. for 1 hour. Crude product which has crystallized is filtered off, washed with cold isopropanol (35 ml) and dried in vacuo. After recrystallization of the crude product from ethyl acetate (150 ml)/cyclohexane (450 ml), 53.2 g (74%) of the title compound are obtained.

m.p.: 138–140° C.

$[a]_D^{20}$+=13.9 (c=1, CHCl$_3$).

We claim:

1. A process for the preparation of enantiomerically pure phenyl-substituted 1,4-dihydropyridine-3,5-dicarboxylic acid compound of the formula

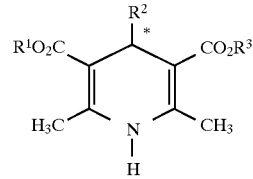

(I)

*R and S in which

R$^1$ and R$^3$ are identical or different and represent straight-chain or branched alkyl having up to 8 carbon atoms which is optionally substituted by straight-chain or branched alkoxy having up to 6 carbon atoms or hydroxyl, or represent cycloalkyl having 3 to 7 carbon atoms, and R$^2$ represents the radical

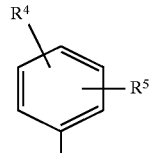

in which

R$^4$ and R$^5$ are identical or different and denote halogen, cyano, ethinyl, trifluoromethoxy, methylthio, nitro, trifluoromethyl or straight-chain or branched alkyl, alkenyl, alkinyl or alkoxy having up to 4 carbon atoms, and one of the substituents optionally represents hydrogen, or a salt thereof, which comprises converting a enantiomerically pure benzylidene compound of the formula (II) or benzylidene compound of the formula (IIa)

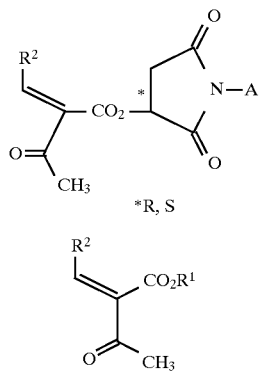
(II)

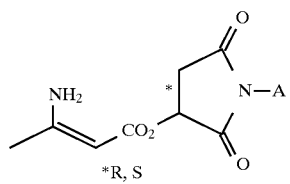
(IIIa)

in which

R¹ and A have the abovementioned meanings in inert solvents, optionally in the presence of a base, to a diastereomerically pure 1,4-dihydropyridine of the formulae (IVa) and (IVb)

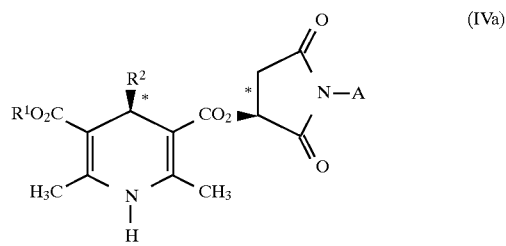
(IVa)

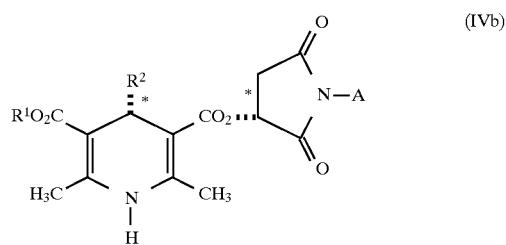
(IVb)

in which

R¹, R² and A have the above-mentioned meanings and the maleimide radical is subsequently eliminated with weak bases under mild conditions, optionally isolating the free acid, and esterifying the carboxyl function.

(IIa)

in which

R¹ and R² have the abovementioned meanings and

A represents hydrogen or straight-chain or branched alkyl having up to 8 carbon atoms, or represents phenyl or benzyl which are optionally substituted one to three times by identical or different substituents from the series consisting of hydroxyl, nitro, halogen, cyano, carboxyl, trifluoromethyl, trifluoromethoxy, straight-chain or branched alkoxy having up to 6 carbon atoms or by a group of the formula —NR⁶R⁷ or —SO₂R⁸ in which

R⁶ and R⁷ are identical or different and denote hydrogen, phenyl or straight-chain or branched alkyl having up to 5 carbon atoms and R⁸ denotes straight-chain or branched alkyl having up to 4 carbon atoms or phenyl, by reaction, in the case of the enantiomerically pure benzylidene compound of formula (II), with aminocrotonic esters of formula (III) and, in the case of the benzylidene compound of the formula (IIa), with the corresponding enantiomerically pure aminocrotonic ester of formula (IIIa)

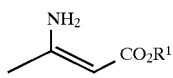
(III)

* * * * *